s010524661B2

United States Patent
Gartenberg et al.

(10) Patent No.: US 10,524,661 B2
(45) Date of Patent: Jan. 7, 2020

(54) SLEEP MONITORING AND STIMULATION

(71) Applicant: ProActive Life, LLC, New York, NY (US)

(72) Inventors: Daniel Gartenberg, Washington, DC (US); Dmitry Gerashchenko, Chestnut Hill, MA (US)

(73) Assignee: Proactive Live, Inc., New York, NY (US)

( * ) Notice: Subject to any disclaimer, the term of this patent is extended or adjusted under 35 U.S.C. 154(b) by 745 days.

(21) Appl. No.: 14/302,482

(22) Filed: Jun. 12, 2014

(65) Prior Publication Data

US 2014/0371547 A1    Dec. 18, 2014

Related U.S. Application Data

(60) Provisional application No. 61/833,922, filed on Jun. 12, 2013, provisional application No. 61/910,418, filed on Dec. 1, 2013.

(51) Int. Cl.
   *A61B 5/00*    (2006.01)

(52) U.S. Cl.
   CPC .......... *A61B 5/0048* (2013.01); *A61B 5/4812* (2013.01)

(58) Field of Classification Search
   CPC ... A61B 5/0048; A61B 5/4812; A61B 5/4809; A61B 5/4815; A61B 5/4818
   See application file for complete search history.

(56) References Cited

U.S. PATENT DOCUMENTS

| | | | | |
|---|---|---|---|---|
| 5,123,425 A | * | 6/1992 | Shannon, Jr. | A61B 5/113 128/848 |
| 5,385,144 A | * | 1/1995 | Yamanishi | A61B 5/02433 600/330 |
| 5,769,084 A | * | 6/1998 | Katz | A61B 5/4818 600/513 |
| 6,811,538 B2 | * | 11/2004 | Westbrook | A61B 5/0205 600/300 |
| 7,469,697 B2 | * | 12/2008 | Lee | A61B 5/0031 128/200.24 |
| 7,578,793 B2 | * | 8/2009 | Todros | A61B 5/0402 600/300 |
| 7,690,378 B1 | * | 4/2010 | Turcott | A61B 5/0816 128/201.23 |
| 7,996,076 B2 | * | 8/2011 | Burns | A61B 5/0488 600/300 |

(Continued)

OTHER PUBLICATIONS

Ngo H.V., Martinetz T., Born J., and Molle M. (2013) Auditory closed-loop stimulation of the sleep slow oscillation enhances memory. Neuron 78, 545-553.

(Continued)

*Primary Examiner* — Lynsey C Eiseman
*Assistant Examiner* — Amanda L Steinberg

(57) ABSTRACT

Sleep monitoring and stimulation comprises collecting actigraphy data from a user. The user's sleep phase is determined using the actigraphy data. At least one stimulation, determined at least in part on the sleep phase, is directed towards the user. Subsequent actigraphy data is collected from the user. The actigraphy data and subsequent actigraphy data is used to determine the user's subsequent sleep phase. The stimulation is modified, based at least in part upon the subsequent sleep phase.

19 Claims, 4 Drawing Sheets

(56) References Cited

U.S. PATENT DOCUMENTS

| | | | | |
|---|---|---|---|---|
| 8,308,661 B2* | 11/2012 | Miesel | ............... | A61B 5/1116 |
| | | | | 600/544 |
| 8,378,832 B2* | 2/2013 | Cassidy | ............ | A61B 5/14551 |
| | | | | 340/573.1 |
| 8,428,726 B2* | 4/2013 | Ignagni | ............... | A61B 5/0488 |
| | | | | 607/42 |
| 2006/0293608 A1* | 12/2006 | Rothman | ............ | A61B 5/0476 |
| | | | | 600/545 |
| 2011/0230790 A1* | 9/2011 | Kozlov | ............... | A61B 5/4812 |
| | | | | 600/595 |
| 2013/0234823 A1* | 9/2013 | Kahn | ................... | A61M 21/02 |
| | | | | 340/3.1 |

OTHER PUBLICATIONS

Ngo H.V., Claussen J.C., Born J., and Molle M. (2013) Induction of slow oscillations by rhythmic acoustic stimulation. J. Sleep Res. 22, 22-31.

Marshall L., Helgadottir H., Molle M., and Born J. (2006) Boosting slow oscillations during sleep potentiates memory. Nature 444, 610-613.

Tononi G., Riedner B.A., Hulse B.K., Ferrarelli F., and Sarasso S. (2010) Enhancing sleep slow waves with natural stimuli. MedicaMundi 54, 73-79.

Marshall L., Molle M., Hallschmid M., and Born J. (2004) Transcranial direct current stimulation during sleep improves declarative memory. J. Neurosci. 24, 9985-9992.

* cited by examiner

SLEEP MONITORING AND STIMULATION

CROSS-REFERENCE TO RELATED APPLICATIONS

This application claims the benefit of U.S. Provisional Application No. 61/833,922, filed on Jun. 12, 2013, entitled "Smartphone-based system for improving sleep and memory," and U.S. Provisional Application No. 61/910,418, filed on Dec. 1, 2013, entitled "Assessment of sleep stages by using actigraphy and sensory stimulation," both which are hereby incorporated by reference in their entirety.

BACKGROUND OF THE INVENTION

Wrist actigraphy may be employed for initial diagnostic of sleep-related pathologies. Actigraphy may support large-scale, population-level sleep research by facilitating inexpensive, unobtrusive measurement across a wide range of circumstances and locations and may provide an opportunity for longitudinal and repeated measures. Wrist actigraphy may be useful for estimating total sleep time and wakefulness after sleep onset. However, wrist actigraphy has at least two major limitations: 1) sleep stages may not be discriminated; and 2) specificity (correctly assigned wake epochs) may be very low. These limitations may be expected because discrimination between N1 to N3 stages of sleep and quiet wakefulness may not be feasible based only on the wrist movements.

DETAILED DESCRIPTION OF EMBODIMENTS

Figure 1:
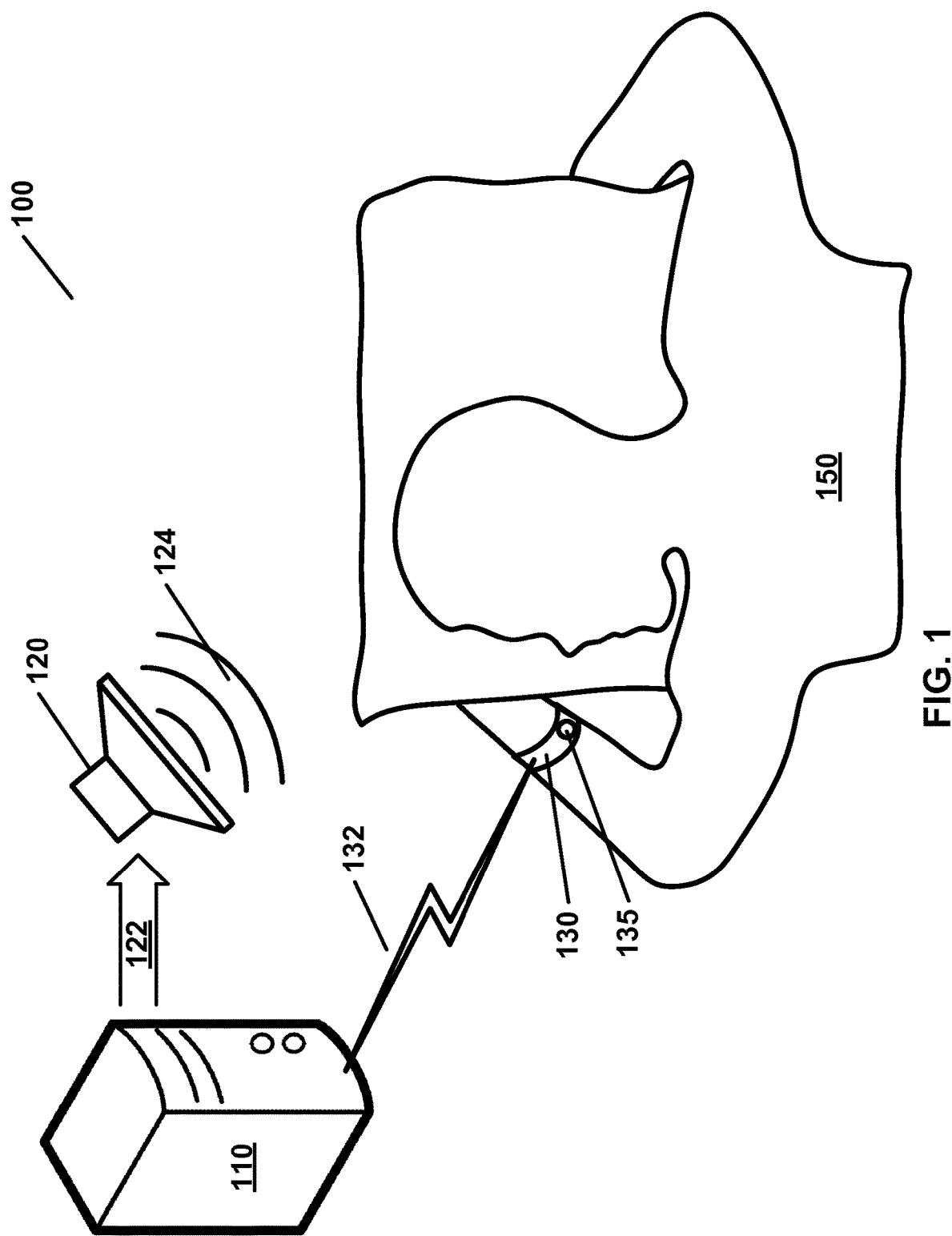
FIG. 1 is an illustration of an example system for sleep monitoring and stimulation as per an aspect of an embodiment of the present invention.

Embodiments of the present invention may employ a combination of actigraphy and stimulation to assess sleep stages. For example, some of the various embodiments may employ auditory stimulation with tones of various intensities, tactile stimulation (e.g., vibration), or other form of sensory stimulation during the sleep period. The sensory stimulation with different characteristics may be generated to induce microarousals and movement of the individual. The microarousals and movement of the individual may be monitored by an actigraphy device (e.g. wrist-worn actigraph, smartphone, or other device). The individual may be instructed to press a button or perform other action to record the microarousal and/or terminate the sensory stimulation. These actions can be performed when consciousness is present during the microarousal. In addition, heart rate, breathing rate and other physiological parameters may be monitored to improve recognition of sleep stages. Sleep stages may be determined based on a combination of these parameters.

Actigraphy systems may be employed as a diagnostic tool for the sleep medicine practitioner, allowing for assessment of sleep over days to weeks in the natural sleep environment outside of the constraints of a laboratory. The systems may typically involve an actigraphy device such as a wrist-watch device containing multi-axis accelerometers that track activity patterns. The actigraphy device may also contain light sensors as an additional signal. Movements may be stored in 30-60 second bins and analyzed according to standard algorithms to allow estimation of wake time (based on a certain magnitude and duration of movements) versus sleep time (based on the relative paucity of movement). Not all actigraphy devices are limited to detection of only body movements, for example, some actigraphy devices may detect other physiological parameters.

Actigraphy may be useful in the detection of sleep efficiency and total sleep time. Standard quantification of rest periods may be performed by actigraphy, including sleep efficiency, total sleep time, and number of movement periods interrupting the rest period. An increased occurrence of movements during a rest period may be an indication of sleep fragmentation. A circadian "amplitude" may be calculated as the ratio of average activity during active periods divided by the average activity during rest periods. Unfortunately, the specification of "sleep" in this methodology may be based entirely on the absence of movement and may not distinguish well quiet wakefulness from sleep, nor may it allow for the distinction of different stages within sleep. Wrist actigraphy may be useful in the documentation of sleep patterns prior to a multiple sleep latency test, in the evaluation of circadian rhythm sleep disorders (delayed circadian phase, advanced circadian phase, irregular sleep—wake syndrome, and/or the like), to evaluate treatment outcomes, and as an adjunct to home monitoring of sleep disordered breathing.

Actigraphy by itself may have poor specificity with regard to detecting wake after sleep onset. There may be some concerns about the validity of sleep-wake scoring in specific populations by actigraphy. For example, comparison of minute-by-minute sleep-wake scorings based on actigraphy and videosomnography in young children found that increasing wakefulness during a sleep period compromises the minute-by-minute actigraphy-polysomnography correspondence because of relatively low specificity of sleep-wake scoring algorithms. It has been concluded that the very low ability of actigraphy to detect wakefulness casts doubt on its validity to measure sleep quality in clinical populations with fragmented sleep. In addition, the validity of actigraphy to detect pathological sleep may be questionable because it does not allow detecting motionless wakefulness which may be common in insomnia and other sleep-related disorders.

Some strategies may be employed to increase specificity of sleep-wake scoring by actigraphy. One such strategy may be the use of a concurrent sleep diary during actigraphy recording. The diary may help differentiate awake but relatively motionless periods from true sleep when interpreting the actigraph data and thus improve the accuracy of sleep-onset identification. The diary may provide a place where a patient can document his/her reasons for napping, arousals, uncharacteristic behavior, and so forth, which may assist a clinician in finding an underlying cause of a sleep disorder. The exact information gathered may depend, in part, on a device used and differential diagnostic considerations. For example, some devices may have an "event marker" that patients may press when getting in and out of bed.

Another strategy to enhance the quality of information from actigraphy may be to include a light sensor on the actigraphy device. This strategy may be useful when there are concerns about the reliability of the diary (e.g., patient is cognitively impaired or may be malingering) or when there may be a need to verify times noted in the sleep diary. Commonly, scorers may use a sharp decrease in light levels near bedtime to help define the major sleep period. Because timed exposure to light may sometimes be used in the treatment of circadian rhythm sleep disorders, a light sensor may also be employed to monitor adherence to light therapy as well.

Although these enhancements may be useful in particular situations, they may not allow a reliable distinction of quiet wakefulness and different stages within sleep.

Auditory stimuli may be processed differently during different stages of sleep. Auditory arousal thresholds during sleep may vary as a function of night, with frequency of awakening increasing across the night. This may be partly explained by the distribution of sleep stages during the night because slow wave sleep (SWS) may dominate the first half of the night when awakenings are reduced and rapid eye movement (REM) sleep may dominate the second half of the night when awakenings are most frequent. In healthy participants, auditory awakening thresholds may be higher in SWS than in stage 2 sleep or REM sleep, with generally comparable thresholds between stage 2 and REM sleep. Auditory awakening thresholds are also known to increase after sleep deprivation when recovery sleep is initiated during the night and may be considered a good indicator of the sleep homeostatic process. Phasic REM sleep may represent a state with maximal environmental shielding (disconnection from the external world), but phasic REM episodes may cover only about 2-3% of total REM sleep time.

Some of the various embodiments distinguish sleep stages in mammals using actigraphy in combination with sensory stimulation during sleep. For example, tones, vibration, or other form of sensory stimulation may be generated either by the external speakers, headphones, smartphone speakers, or other sound-generating device and used to probe different sleep stages. Sensory stimulation of different intensity may be delivered throughout sleep in humans or animals. Such sensory stimulation may cause movements and changes in certain physiological parameters (e.g. heart rate, breathing rate, blood pressure, etc.). The movement and physiological parameters resulting from the sensory stimulation may be monitored to determine the likely sleep stage. The probing may be repeated during a sleep period (e.g. night time) to determine sleep stages with an increased level of confidence. The sensory stimulation may produce brief periods of awakening or shifts in sleep phase, so most or all awakenings may not be remembered. Some of the various embodiments may comprise a calibration stage whereby sensory stimulation, actigraphy, and physiological parameters are monitored until a given threshold is reached. After the calibration stage is finished, processed actigraphy data may be generated by augmenting collected actigraphy data by the thresholding data. The processed actigraphy data may be employed to predict sleep stage(s). Actigraphy data collected and/or processed from prior sleep sessions may be employed by embodiments to predict sleep stage(s).

FIG. 1 is an illustration of an example system for sleep monitoring and stimulation as per an aspect of an embodiment of the present invention that includes a wrist actigraphy device 130 (e.g. bracelet or watch), an audio stimulation device 120 (e.g. earphone or external speaker), and a processing device 110. According to some of the various embodiments, bracelet 130 may contain an accelerometer, a heart rate monitoring device, a microphone to record special events, and/or the like.

Before sleep, the wrist actigraphy device 130 may be worn on the wrist, and the audio stimulation device 120 placed within range of an individuals' ear. System 100 functionality may be initiated by a computer program executing on processing device 110, bracelet 130 and the audio stimulation device 120. The wrist actigraphy device 130 may monitor body movements by actigraphy and communicate this information to the processing device 110 via a communications link 132 (e.g. BLUETOOTH™). Heat rate data may also be monitored and communicated to the processing device 110. The computer program may determine a period of inactivity and start triggering brief tones on the audio stimulation device via link 122. The period of inactivity may be, for example, 15-20 min. However, those skilled in the art will recognize that other time intervals may also be employed. If wrist movement is not detected, the tone may be delivered at a higher volume in a short period of time. This procedure may be repeated several times. If the tone is heard during wakefulness, according to some of the various embodiments, the subject may press the button 135 on the bracelet 130 to cause the processing device 110 to stop the stimulation. According to some of the various embodiments, the stimulation may be stopped by moving. Tactile stimulation (vibrations) or any other form of sensory stimulation may also be delivered according to the same procedure.

Some of the various embodiments, as compared with actigraphy alone may improve detection of sleep stages. For example, SWS may not be reliably distinguished from other sleep stages by only actigraphy. Tactile or auditory stimulation may assist in determining SWS because sensory arousal thresholds are highest during this stage of sleep, so that micro-arousals are not expected to be induced by vibration or tones during SWS. Embodiments may improve wake detection. Brief wakefulness episodes may remain undetected by actigraphy alone if an individual 150 does not move in bed during such episodes. However, the individual may be instructed to press a button 135 on the wrist-worn device 130 (or, according to some embodiments, make a detectable movement) if vibration is felt or tones are heard during wakefulness episodes. Micro-arousals may be induced by sensory stimulation during light phases of sleep. Therefore, embodiments may be employed to detect fragmented or pathological sleep because these forms of sleep may be greater during light sleep phases.

Tones may be generated via an audio stimulation device 120 such as, for example, earphones, headphones, external speakers, and/or the like. The frequency of auditory stimulation 124 and/or vibration may be based on studies, such as the alarm signaling studies commissioned by the U.S. Fire Administration and the Fire Protection Research Foundation, an affiliate of the National Fire Protection Association. These studies demonstrated that a 520 Hz square-wave signal may be effective at waking heavy sleepers. However, one skilled in the art will recognize that other frequency of auditory stimulation and vibration may also be employed, for example, a low frequency vibration in a range of approximately one or less hertz.

Some of the various embodiments may be used in clinics to assess sleep quality. Embodiments may also be employed by individual(s) who may be interested in a rapid and inexpensive way of determining their sleep pattern(s). Moreover, embodiments may be employed in research studies in both humans and animals.

Figure 2:
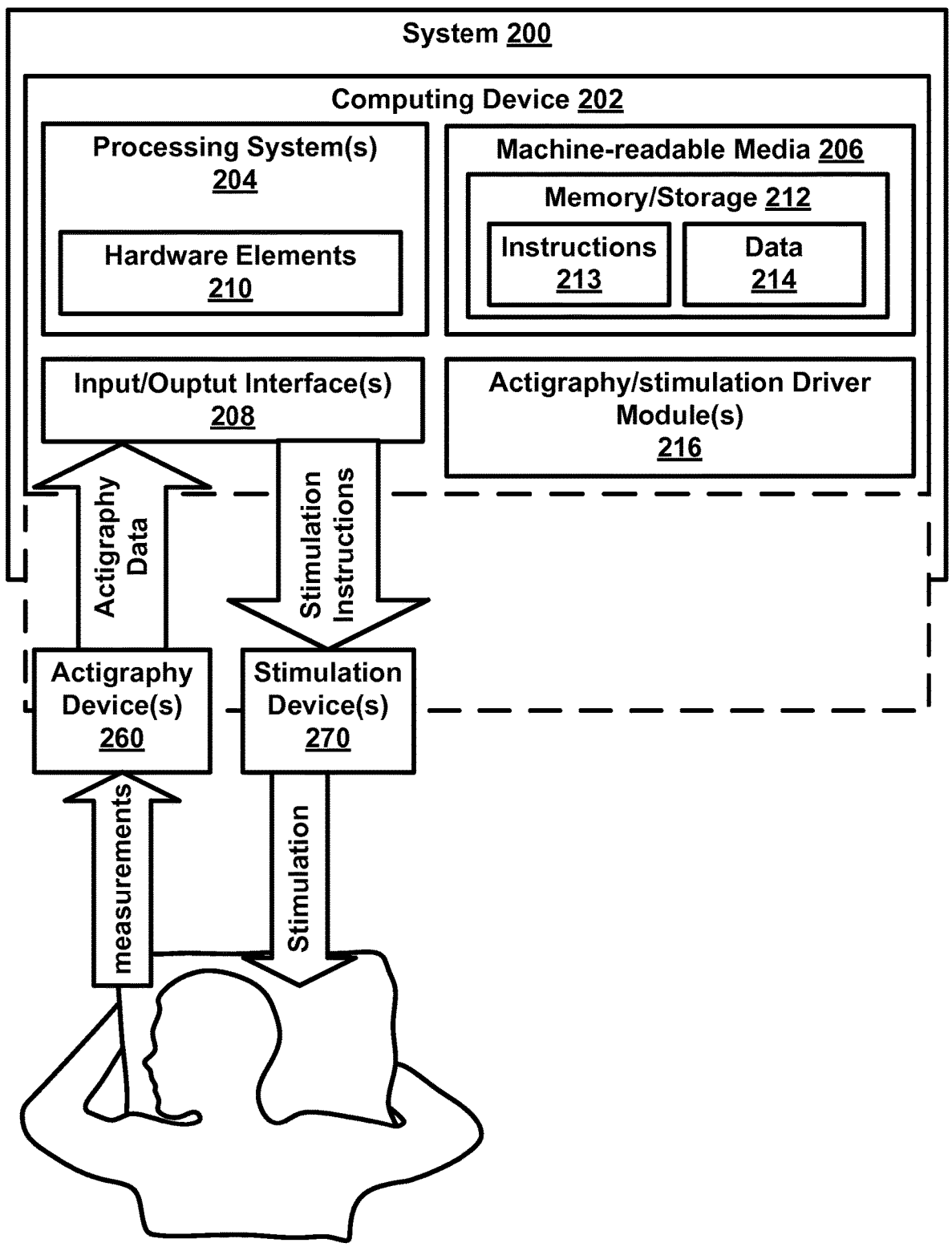
FIG. 2 is a block diagram of an example system for sleep monitoring and stimulation as per an aspect of an embodiment of the present invention.

FIG. 2 illustrates an example sleep monitoring and stimulation system 200 that includes an example computing device 202 that is representative of one or more computing systems and/or devices that may implement the various techniques described herein. The computing device 202 may be, for example, a server of a service provider, a device associated with a client (e.g., a client device), an on-chip system, and/or any other suitable computing device or computing system.

The example computing device 202 as illustrated includes a processing system 204, one or more machine-readable media 206, and one or more Input/Output interface(s) 208 that are communicatively coupled, one to another. Although not shown, the computing device 202 may further include a system bus or other data and command transfer system that couples the various components, one to another. A system bus may comprise any one or combination of different bus structures, such as a memory bus or memory controller, a peripheral bus, a universal serial bus, a processor or local bus and/or the like that utilizes any of a variety of bus architectures. A variety of other examples are also contemplated, such as control and data lines.

The processing system 204 may be representative of functionality to perform one or more operations using hardware. Accordingly, the processing system 204 is illustrated as including hardware elements 210 that may be configured as processors, functional blocks, and so forth. This may include implementation in hardware as an application specific integrated circuit or other logic device formed using one or more semiconductors. The hardware elements 210 may not be limited by materials from which they are formed or the processing mechanisms employed therein. For example, processors may be comprised of semiconductor(s) and/or transistors (e.g., electronic integrated circuits (ICs)). In such a context, machine-executable instructions may be electronically-executable instructions by devices such as electronic processors.

The machine-readable media 206 is illustrated as including memory/storage 212. The memory/storage 212 represents memory/storage capacity associated with one or more machine-readable media. The memory/storage 212 may include volatile media (such as random access memory (RAM)) and/or nonvolatile media (such as read only memory (ROM), Flash memory, optical disks, magnetic disks, and so forth). The memory/storage 212 may include fixed media (e.g., RAM, ROM, a fixed hard drive, and so on) as well as removable media (e.g., Flash memory, a removable hard drive, an optical disc, and so forth). The machine-readable media 206 may be configured in a variety of other ways as further described below.

The memory/storage 212 may include machine readable instructions 213 and data 214. The machine readable instructions 213 may be configured to cause one or more processors within the processing system 204 to complete a multitude of actions as described herein. The processors may be dedicated or shared, virtual or real, and/or the like. Virtual processors may run on a hardware processor as an isolated process. Data 214 may store variables, data over input/output interface(s) 208, and/or the like.

Input/output interface(s) 208 may be representative of functionality to allow a user to enter commands and information to computing device 202, and also allow information to be presented to the user and/or other components or devices using various input/output devices. Examples of input devices include a keyboard, a cursor control device (e.g., a mouse), a microphone for voice operations, a scanner, touch functionality (e.g., capacitive or other sensors that are configured to detect physical touch), a camera (e.g., which may employ visible or non-visible wavelengths such as infrared frequencies to detect movement that does not involve touch as gestures), and so forth. Examples of output devices include a display device (e.g., a monitor or projector), speakers, a printer, tactile-response device, and so forth. Computing device 202 may further include various components to enable wired and wireless communications including for example a network interface for network communication and/or various antennas to support wireless and/or mobile communications. A variety of different types of suitable antennas are contemplated including, but not limited to, one or more Wi-Fi antennas, global navigation satellite system (GNSS) or global positioning system (GPS) antennas, cellular antennas, Near Field Communication (NFC) antennas, BLUETOOTH™ antennas, and/or so forth. Thus, computing device 202 may be configured in a variety of ways as further described below to support user interaction.

According to some of the various embodiments, input/output interface(s) 208 may be configured to communicate with actigraphy device(s) 260, stimulation device(s) 270, and/or the like. The input/output interface(s) may include the communication between the computing device 202 and internal components such as, but not limited to, processing system(s) 204. The communications with the actigraphy device(s) 260 and/or stimulation device(s) 270 may be via a wired and/or wireless interface. Examples of wired interfaces include Ethernet, RS-232. RS-422, Universal Serial Bus (USB), FireWire™, and/or the like. Examples of wireless interfaces include BLUETOOTH™, 802.11, WiFi, Cellular, and/or the like. Actigraphy and/or stimulation driver module(s) 216 may be employed to effectuate communications between the computing device 202 and the actigraphy device(s) 260 and/or stimulation device(s) 270. The driver module(s) 216 may comprise machine executable instructions that operate or control the actigraphy device(s) 260 and/or stimulation device(s) 270 attached to the computing device 202. A driver 216 may provide a software interface to hardware device(s) 260 and/or 270, enabling operating systems and other computer programs to access hardware functions without needing to know precise details of the hardware being used. A driver 216 may communicate with the device(s) 260 and/or 270 through the computer bus or communications subsystem to which the hardware connects. When a calling program invokes a routine in the driver 216, the driver 216 may issue commands to the actigraphy device(s) 260, and/or stimulation device(s) 270. Once the actigraphy device(s) 260, and/or stimulation device(s) 270 send data back to the driver 216, the driver 216 may invoke routines in the original calling program. Drivers 216 may be hardware-dependent and operating-system-specific. Drivers 216 may provide the interrupt handling required for any necessary asynchronous time-dependent hardware interface.

According to some of the various embodiments, actigraphy device(s) 260, and/or stimulation device(s) 270 may be embedded in computing device 202. For example, in an embodiment where computing device 202 is a smartphone, stimulation device 270 may be the speaker built into the smartphone. According to some of the various embodiments, actigraphy device(s) 260, and/or stimulation device(s) 270 may be external to computing device 202. For example, in an embodiment where computing device 202 is a smartphone, stimulation device 270 may be an external speaker connected to the computing device 202 via the headphone jack, a BLUETOOTH™ connection, a combination thereof, and/or the like. This variation in embodiments is illustrated in FIG. 2 with computing device 202 shown with a lower dashed line representing actigraphy device(s) 260 and/or stimulation device(s) 270 may be located in or out of computing device 202.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software in combination with hardware, firmware, hardware, a combination thereof, and/or the like. The features of the techniques described herein may be platform-independent, meaning that the techniques may be implemented on a variety of commercial computing platforms having a variety of processors. However, one skilled in the art will recognize that the features of the techniques described herein may also be implemented on a variety of custom platforms.

An implementation of the described modules and techniques may be stored on or transmitted across some form of machine-readable media. The machine-readable media may include a variety of media that may be accessed by computing device 202. By way of example, and not limitation, machine-readable media may include "machine-readable storage media" and "communication media."

"Machine-readable storage media" refers to media and/or devices that enable storage of information in contrast to mere signal transmission, carrier waves, or signals per se. Thus, machine-readable storage media does not include signal bearing media or signals per se. The machine-readable storage media may comprise hardware such as volatile and non-volatile, removable and non-removable media and/or storage devices implemented in a method or technology suitable for storage of information such as computer readable instructions, data structures, program modules, logic elements/circuits, or other data. Examples of machine-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage devices, tangible media, or articles of manufacture suitable to store the desired information and which may be accessed by a computing device 202.

"Communication media" refers to signal-bearing media configured to transmit instructions to the hardware of the computing device 202, such as via a network. Communication media typically may embody computer readable instructions, data structures, program modules, or other data in a modulated data signal, such as carrier waves, data signals, or other transport mechanism. Communication media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 210 and machine-readable media 206 are representative of instructions, modules, programmable device logic and/or fixed device logic implemented in a hardware form that may be employed in some embodiments to implement at least some aspects of the techniques described herein. Hardware elements may include components of an integrated circuit or on-chip system, an application-specific integrated circuit (ASIC), a field-programmable gate array (FPGA), a complex programmable logic device (CPLD), and other implementations in silicon or other hardware devices. In this context, a hardware element may operate as a processing device that performs program tasks defined by instructions, modules, and/or logic embodied by the hardware element as well as a hardware device utilized to store instructions for execution, e.g., the machine-readable storage media described previously.

Combinations of the foregoing may also be employed to implement various techniques and modules described herein. Accordingly, software, hardware, or program modules including driver module(s), device application(s), and other program modules may be implemented as one or more instructions and/or logic embodied on some form of machine-readable media and/or by one or more hardware elements 210. Computing device 202 may be configured to implement particular instructions and/or functions corresponding to the software and/or hardware modules. Accordingly, implementation of modules as a module that is executable by computing device 202 as software may be achieved at least partially in hardware, e.g., through use of machine-readable storage media and/or hardware elements 210 of the processing system. The instructions and/or functions may be executable/operable by one or more articles of manufacture (for example, one or more computing devices 202 and/or processing systems 204) to implement techniques, modules, and examples described herein.

As further illustrated in FIG. 2, the example system 200 may enable ubiquitous environments for a seamless user experience when running applications on a personal computer (PC), a television device, a mobile device, a combination thereof, and/or the like. Services and applications may run substantially similar in various environments for a common user experience when transitioning from one device to the next while utilizing an application, playing a video game, watching a video, sleeping, and so on.

In the example system 200, multiple devices may be interconnected through a central computing device. The central computing device may be local to the multiple devices or may be located remotely from the multiple devices. In one embodiment, the central computing device may be a cloud of one or more server computers that are connected to the multiple devices through a network 320, the Internet, or other data communication link.

In one embodiment, this interconnection architecture enables functionality to be delivered across multiple devices to provide a common and seamless experience to a user of the multiple devices. Each of the multiple devices may have different physical requirements and capabilities, and the central computing device may use a platform to enable the delivery of an experience to the device that is both tailored to the device and yet common to all devices. In one embodiment, a class of target devices may be created and experiences tailored to the generic class of devices. A class of devices may be defined by physical features, types of usage, or other common characteristics of the devices.

In various implementations, the computing device 202 may assume a variety of different configurations, such as for a computer, a mobile device, and a smart device, a dedicated device, and/or the like. Each of these configurations may include devices that may have generally different constructs and capabilities, and thus computing device 202 may be configured according to one or more of the different device classes. For instance, computing device 202 may be implemented as a computer class of a device that includes a personal computer, desktop computer, multi-screen computer, laptop computer, netbook, and so on.

The computing device 202 may also be implemented as, for example, a mobile class of device that may include mobile devices, such as, for example, a mobile phone, portable music player, portable gaming device, a tablet computer, a multi-screen computer, and so on. The computing device 202 may also be implemented as a television class of device that includes devices having or connected to generally larger screens in casual viewing environments. These devices may include television, set-top boxes, gaming consoles, and so on.

The techniques described herein may be supported by these various configurations of the computing device 202 and are not limited to the specific examples of the techniques described herein. This is possible, for example, by including specific support as illustrated through inclusion of the actigraphy driver module 216 on computing device 202. The functionality of the actigraphy driver module 216 and other modules may also be implemented all or in part through use of a distributed system, such as over a "network" 322 via a platform 322 as described below.

Figure 3:
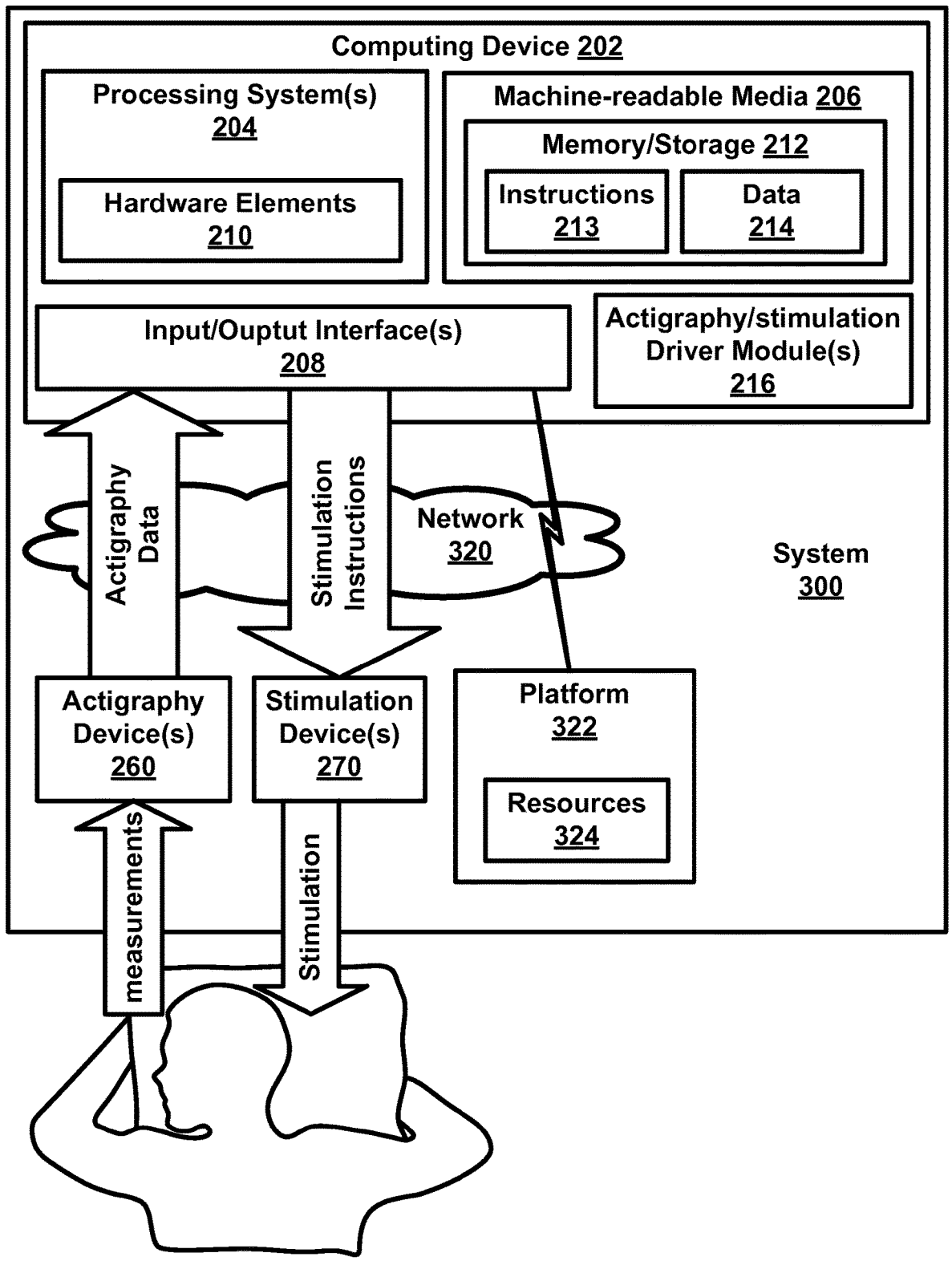
FIG. 3 is a block diagram of an example system for sleep monitoring and stimulation that employs a network as per an aspect of an embodiment of the present invention.

FIG. 3 illustrates a system 300 for sleep monitoring and stimulation that employs a network 320 as per an aspect of an embodiment of the present invention. As illustrated, network 320 may communicatively connect one or more devices such as, but not limited to, computing device(s) 202, actigraphy device(s) 260, stimulation device(s) 270, mobile devices, and/or the like.

Network 320 may be part of a larger "cloud" that connects multiple devices such as, for example, one or more servers, devices, and/or the like through one or more other networks, the Internet, other data communication link, and/or the like. Platform 322 abstracts underlying functionality of hardware (e.g., servers) and software resources that may be available on the network 320 and/or cloud. The resources 324 may include applications and/or data that can be utilized while computer processing is executed on servers that are remote from the computing device 202. Resources 324 may also include services provided over the Internet and/or through a subscriber network, such as a cellular or Wi-Fi network.

The platform 322 may abstract resources and functions to connect the computing device 202 with other computing devices. The platform 322 may also serve to abstract scaling of resources to provide a corresponding level of scale to encountered demand for the resources 324 that may be implemented via the platform 322. Accordingly, in an interconnected device embodiment, implementation of functionality described herein may be distributed throughout the system 300. For example, the functionality may be implemented in part on the computing device 202 as well as via platform 322 that abstracts the functionality.

Figure 4:
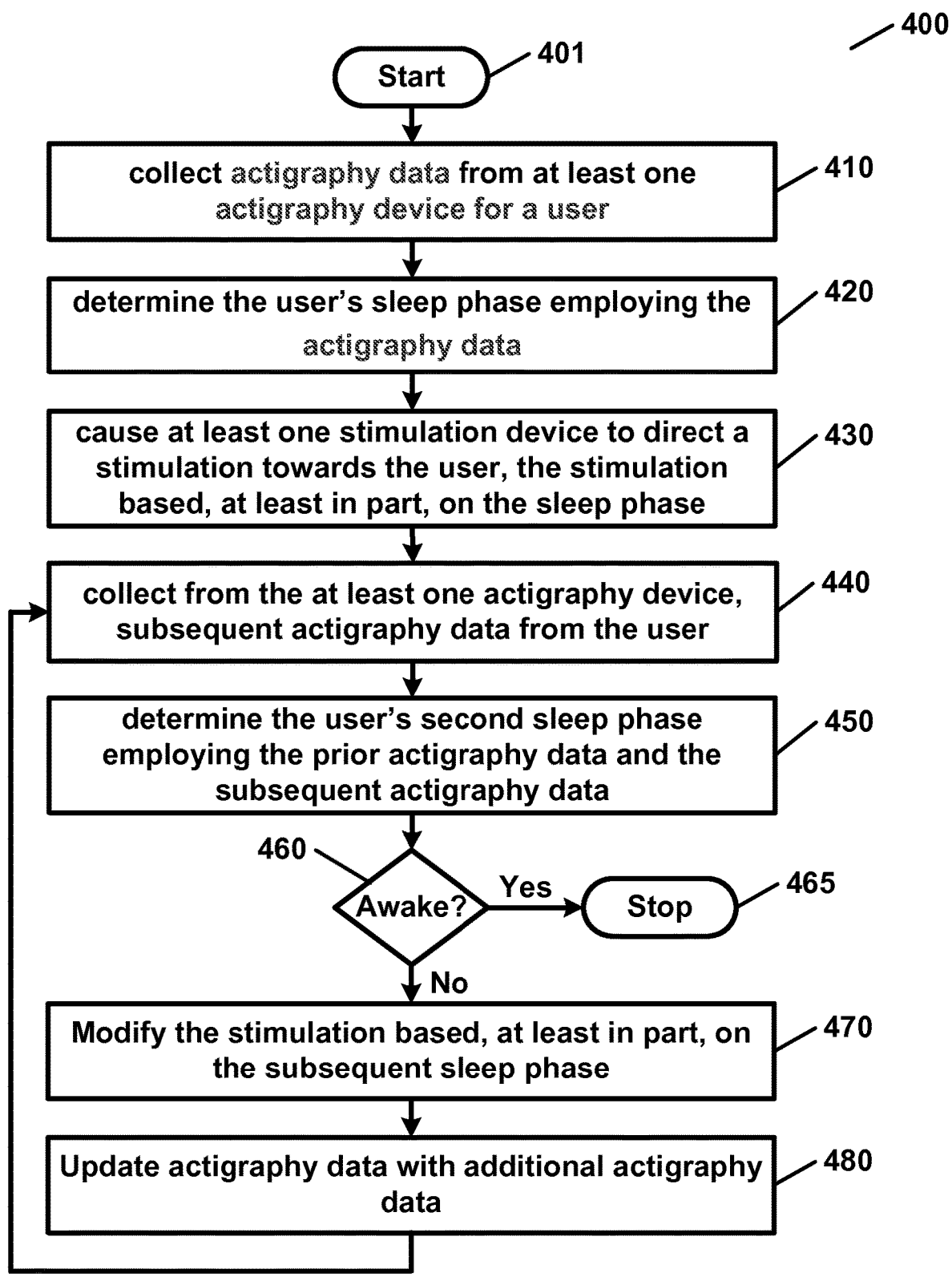
FIG. 4 is a flow diagram of a technique of sleep monitoring and stimulation as per an aspect of an embodiment of the present invention.

FIG. 4 is a flow diagram 400 of a technique of sleep monitoring and stimulation as per an aspect of an embodiment of the present invention. The techniques described in the flow chart of FIG. 4 may be implemented in various configurations employing a system, an apparatus, a method, a non-transitory computer readable storage medium, and/or the like. For example, according to one of the various embodiments, the non-transitory computer readable storage medium may comprise machine executable instructions configured to cause one or more processors to perform the techniques described herein including the actions of flow diagram 400. According to another of the various embodiments, the techniques described in flow diagram 400 may be applied to an apparatus such as, but not limited to, computing device 202 shown in FIG. 2 and/or FIG. 3 and described above. According to yet another of the various embodiments, the techniques described in flow diagram 400 may be applied to a system such as, but not limited to, system 200 disclosed in FIG. 2 and/or system 300 disclosed in FIG. 3 and described above. According to yet another of the various embodiments, the techniques described in flow diagram 400 may be applied as a method employing devices such as, but not limited to, actigraphy device(s) 260 and stimulation device(s) 270 described above.

The actions of flowchart 400 may be activated at 401. The activation may be initiated when starting sleep. Depending upon the embodiment, the process may be activated by starting a machine executable program on a processing device. The activation may be initiated via a sensor on one of the devices (e.g. actigraphy device) connected to the processing device or on the processing device directly. According to some embodiments, the processing device may be a mobile device such as a smartphone, a tablet computer, and/or the like. In one of these embodiments, the program may be initiated via a user graphical interface.

At 410, actigraphy data from a user may be collected from at least one actigraphy device. An actigraphy device, or actimetry sensor(s), may be worn on, for example, the arm, leg, torso, head, and or the like to measure body movement. According to some of the various embodiments, the actigraphy device may be worn on the wrist. Examples of actigraphy devices include the Fitbit (available from Fitbit of San Francisco Calif.), the WakeMate (available from Perfect Third Inc of San Francisco Calif.), and the Nike Fuel Band (available from Nike Inc of Washington, Oreg.). An actigraphy device may consist of: a piezoelectric accelerometer, a low-pass filter, a timer, and a memory to store data.

Actigraphy data may comprise body movement data sampled at a rate configured to capture gross body movements. An example sampling rate is typically at a rate of at least 2-3 Hertz. Raw actigraphy data may pass through a low-pass filter in order to prevent vibrations from affecting movement data.

Sleep stage(s) may comprise light sleep (N1), intermediate sleep (N2), deep sleep (N3), awakenings, and REM sleep. Non-REM (NREM) sleep can be broken down into three distinct stages: N1, N2, and N3. In the progression from stage N1 to N3, brain waves may become slower and more synchronized and the eyes may remain still. N1 is considered to be light sleep and N3 may be considered to be the deepest stage of NREM sleep.

Because individuals may naturally wake up and go through different stages of sleep throughout the night, an individual's sleep phase may be determined at 420 employing the actigraphy data. Sleep phases may comprise at least one of the following: REM sleep phase; N1 sleep phase; N2 sleep phase; N3 sleep phase; a light sleep phase; a deep sleep phase; and an awake phase.

According to some of the various embodiments, zero-crossing threshold detection may be applied to processed actigraphy data to calculate a period (e.g. approximately 10 seconds) of each minute with the largest integrated acceleration. This may result in each minute being associated with a maximum number of zero-crosses, known as counts. Each minute may be categorized as sleep/wake by taking a weighted average of several minutes (e.g. approximately 4 minutes) before the current minute, the current minute, and approximately two minutes after the current minute as predictors. For example, the actigraphy data may be analyzed according to a logistic regression equation to predict sleep/wake. An example logistic regression equation is: $D=P(0.010(A-4)+0.015(A-3)+0.028(A-2)+0.031(A-1)+0.085(A0)+0.015(A+1)+0.010(A+2))$. If D is determined to be greater than or equal to 1, the minute may be determined as awake. P may be employed as a scaling factor for the polynomial. A may represent the minute, where, for example, A−4 is the activity score for four minutes before the current minute, etc.

Because sleep may be similar from night to night and typically follows the pattern of: light sleep, deep sleep, light sleep, REM sleep—with a greater proportion of deep sleep earlier in the night—the stage of sleep may be estimated from the actigraphy data. The stage of sleep may be estimated from the sleep stage data based on how long sleep has occurred. This may comprise categorizing sleep based on when it occurs, where the sleep phase may be categorized as deep sleep with a greater likelihood if the sleep occurs in the beginning of the night. This may also comprise determining a light sleep phase before and after an awakening and a deep sleep phase after an awakening.

Actigraphy data may comprise body motion data. However, according to some of the various embodiments, the actigraphy data may be enhanced with physiological parameters such as, but not limited to: breathing rate data; heart rate data; sound data; blood pulse data; blood pressure data; temperature data; blood oxygenation data; perspiration data; electromyography data; electroencephalography data; a combination thereof; and/or the like.

Various devices may be employed for measurements of heart rate. These include different types of heart rate monitors, such as chest strap models that consist of a chest strap that fastens around the chest and wirelessly transmits continuous heart rate data to a receiver. In strapless models, heart rate may be measured by electrocardiography. In this case, electrical activity may be measured from pads and electrodes that fit on an individual's extremities and/or chest. Other devices to measure heart rate include pulse oximetry that use a probe fit to the finger or earlobe or Doppler ultrasound that measures ultrasound waves and Doppler's effect and fit somewhere on the skin lying over an artery such as over the radial or ulnar artery.

Pulse oximetry may provide a non-invasive and comparatively inexpensive method of continuously monitoring oxygenated haemoglobin in blood based on the differential light absorption properties of oxygenated and deoxygenated haemoglobin. Pulse oximetry may provide an accurate measure of both heart rate and oxygen saturation. Signal analysis techniques may permit the determination of the respiratory rate from the plethysmogram produced by a standard pulse oximeter. Heart rate and respiration may be monitored through a small patch worn on the chest, transferring the information to an external device. For example, rainbow Acoustic Monitoring™ (available from Masimo Corporation of Irvine, Calif.) may continuously measure respiration rate using an adhesive sensor with an integrated acoustic transducer that may be applied to the individual's neck.

The body temperature of an individual may vary depending on gender, recent activity, food and fluid consumption, time of day, the stage of the sleep cycle, and/or the like. Body temperature may differ depending on the mechanism employed to measure the temperature (e.g., orally, rectally, axillary, by ear, by skin). The body temperature may be declining during progression to deeper sleep stages. Determining changes in temperature, rather than absolute values, may be helpful in determining sleep stages. Various embodiments may be configured to employ many types of thermometer(s) that allows measurements of body temperature, such as thermoelectric thermometers, infrared thermometers, thermal image cameras, and/or the like.

According to some of the various embodiments, for example, sound data may be measured using a microphone, a piezoelectric crystal configured to measure vibrations, a sound recorder, a smart device, combinations thereof, and/or the like. Sound data may include the sound of a user snoring. Snoring may be indicative of an individual sleep phase.

According to some of the various embodiments, a location device such as, for example, a GPS device, a triangulation device, and/or the like may be employed to determine when a person is in their own sleep area (e.g. bedroom), or in a different sleep area. For example, it may be useful to know if a person is sleeping on a couch, in a hotel, at a friend's house, and/or the like. Embodiments may take account of and/or record data based on locations. The location device may be employed to determine a person's bedtime. For example, if a person moves from a living room to a bedroom, this may be an indication that they are preparing to go to sleep. Similarly, travel from a bedroom to a kitchen, may indicate that they have awakened. As described, actigraphy may be used for estimating total sleep time and wakefulness after sleep onset. However, enhancing the actigraphy with physiological parameters may help discriminate sleep stages with a higher level of certainty. These enhancements may improve discrimination between sleep stages because, for example, the N1 and N2 stages of sleep and quiet wakefulness may be difficult to achieve based only on body movements. The determination of N3 stage of sleep based on actigraphy data may be performed with a higher degree of certainty because body movement may be lowest during this stage of sleep compared to other sleep stages. Nevertheless, some errors may be expected when N3 stage of sleep is determined by actigraphy alone. Assessment of heart rate, respiration and other physiological parameters during sleep may improve recognition of sleep stages and reduce errors in the determination of sleep stages.

At 430, at least one stimulation device may direct a stimulation towards the user. The stimulation may be determined, at least in part, on the sleep phase. Stimulation may be configured to stimulate one or more senses. Senses are physiological capacities of organisms that provide data for perception. A sense may be considered as a system of sensory cell types that responds to a specific physical phenomenon and that corresponds to a particular group of regions within the brain where the signals are received and interpreted.

Humans have a multitude of senses. Sight (ophthalmoception), hearing (audioception), taste (gustaoception), smell (olfacoception or olfacception), and touch (tactioception) are the five traditionally recognized senses. Additional senses may include the ability to detect other stimuli beyond those governed by the traditional senses, including, but not limited to: temperature (thermoception), kinesthetic sense (proprioception), pain (nociception), balance (equilibrioception), and various internal stimuli (e.g. the different chemoreceptors for detecting salt and carbon dioxide concentrations in the blood). Some species of animals may be able to sense the world in a way that humans cannot, with some species able to sense electrical and magnetic fields, polarized light, water pressure, water currents, and/or the like.

To effectuate the stimulation, the stimulation device may be configured to generate specific physical phenomenon(s) to stimulate sensory cell types that in response will send signals to the brain. Examples of stimulations include, but are not limited to: auditory stimulation, a tactile stimulation, electrical stimulation, neuro-stimulation; transcranial direct current stimulation; light stimulation; odor stimulation; a combination of the above, and/or the like.

Some of the various embodiments may deliver stimulations (e.g. auditory, tactile, and/or the like) during the night and record actigraphy data, heart rate and other physiological responses to the stimulation. The responses may differ during different stages of sleep. For example, minimal movement may be expected in response to auditory stimulation during slow-wave sleep because auditory thresholds may be the highest during this stage of sleep. On the contrary, individuals may be aroused by auditory stimulation during lighter stages of sleep (N1 and N2), and the resulting micro-arousals may be expected to be associated with movement responses. Micro-arousals may be brief periods of wakefulness during which consciousness may be or may not be present. Body movements may occur during micro-arousals. The periods of sensory stimulation may be brief and delivered repeatedly during the night (for example, a few seconds of stimulation repeated several times at the ascending intensity delivered every 15 or 20 minutes after motionless is detected by actigraphy). Brief sensory stimulation may not be expected to greatly disturb sleep or be remembered because individuals may be essentially "amnesic" in sleep. For example, human participants presented with a mean of 200 tones and made a mean of 49 micro-switch closures to them, only recalled a mean of 3.5 tone presentations and a mean of 3.2 microswitch closures. Moreover, such presentation of tones resulted in only little disruption of sleep. Motor responses to external stimuli may occur during sleep without conscious awareness or complete awakening, allowing induction of movement by tones without awakening the individual.

The volume or intensity of stimulation may be increased until a triggering of movement or changes in heart rate, breathing, or other physiological parameters occurs. The stimulation may be stopped or the stimulation intensity reduced. Stimulation may be employed to invoke several responses. For example, according to some of the various embodiments, stimulation may be employed to enhance SWS or determine a stage of sleep. In the latter case, the stimulation may be performed during brief periods, so that the sleep pattern would not be significantly changed. According to some other embodiments, stimulation may be employed for other purposes, such as, for example, inducing dreams, inducing moving from N1 to N2, inducing moving from N2 to N3, preventing snoring, preventing night terrors, identifying sleep disorders, and/or the like.

Auditory stimulation may be generated using a speaker. The speaker may be connected to an audio signal generating device such as a computer, a smartphone, and/or the like. Tactile stimulation may be generated using low frequency sound waves generated via an audio speaker, a shaker, a mechanical actuator, and/or the like. Tactile stimulation may also be generated using a haptic device. A haptic device may be a tactile technology which recreates the sense of touch by applying forces, vibrations, or motions to an individual. Electrical stimulation may be applied using a device such as a transcutaneous electrical nerve stimulation (TENS) device which uses electric current to stimulate nerves. TENS units may be connected to the skin using two or more electrodes. The electrical stimulation may be configured to modulate pulse width, frequency and/or intensity of the electrical stimulation. Neuro-stimulation (and/or Transcranial direct current stimulation (tDCS)) may employ current delivered directly to a brain area of interest via small electrodes. Neuro-stimulation, originally developed to help patients with brain injuries such as strokes, may be applied to some of the various embodiments as a stimulation to determine sleep phase. Light stimulation may involve modulating light in a room. Modulation may involve, for example, changes in intensity and/or flashing of a light. Odor stimulation may be effectuated using an odor generator. For example, U.S. Pat. No. 8,469,293 to Doty et al. discloses a digital odor generator that may be employed to expose an individual to one or more odorants during a sleep period.

According to some of the various embodiments, stimulation may comprise a multitude of stimulations. In other words, a stimulation may involve a series of stimulations by a single stimulation device and/or a stimulation may include stimulations from a multitude of stimulation devices. For example, an auditory stimulation may involve a series of auditory stimulations at various frequencies. This may be useful if an individual, for example, may have hearing loss at unknown frequencies. In another example, an auditory stimulation may be accompanied by a vibration. The added stimulation may again be useful to account for a potential hearing loss in, for example, an older individual. In yet another example, a sequence of stimulations by various stimulation devices may be employed to determine what effect each stimulation type may have on the individual, possibly during various phases of sleep. Some embodiments may comprise a multitude of stimulations where one of the multitude of stimulations comprises at least one inactive stimulation. An inactive stimulation may include a highly attenuated stimulation.

At 440, some of the various embodiments may collect subsequent actigraphy data from the user employing the actigraphy device(s). As used herein, subsequent actigraphy data may be collected after a stimulation in a similar manner as described above with reference to collecting actigraphy data before a stimulation. At 450, an individual's subsequent sleep phase may be determined employing techniques described above as applied to actigraphy data from previous measurement cycles in combination with the subsequent actigraphy data.

If it is determined at 460 that the individual has awakened from their sleep, or that the stimulation has disturbed sleep, and the sleep monitoring and stimulation is no longer necessary, the process may be terminated at 465. At 470, the stimulation(s) may be modified based, at least in part, on the subsequently determined sleep phase. Modifications to the stimulation(s) may be made at various times. For example, stimulation(s) may be modified within a sleep phase, when the actigraphy data indicates that the user may have changed sleep phases, when the actigraphy data indicates that the user may be waking, at a predetermined or calculated time within a sleep phase, a combination thereof, and/or the like.

According to some of the various embodiments, the actigraphy data may be updated to include subsequent actigraphy data at 480 and the process continued for an additional cycle starting at 440. The cycles may continue throughout a sleep period until the individual's sleep cycle is complete (determined in some of the various embodiments at 460).

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e hardware with a biological element) or a combination thereof, all of which are behaviorally equivalent. For example, modules may be implemented using computer hardware in combination with software routine(s) written in a computer language (such as C, C++, Fortran, Java, Basic, Matlab or the like) or a modeling/simulation program such as Simulink, Stateflow, GNU Octave, or LabVIEW MathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) monitoring human sleep. However, one skilled in the art will recognize that embodiments of the invention could be employed to assist humans in memory retention, assist animals, for example, cats, dogs, horses, and/or the like with sleep.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method comprising:
   estimating an initial sleep phase;
   determining an inactivity period comprising a period of fifteen to twenty minutes;
   causing at least one stimulation device to direct an increasing intensity of stimulation towards a user in response to the inactivity period, wherein the stimulation is:
      determined, at least in part, by the initial sleep phase to induce a micro-arousal without altering a sleep pattern associated with the initial sleep phase; and
      applied externally as at least one of a tactile stimulation and an auditory stimulation for one to five seconds;
   in response to the increasing intensity of stimulation:
      collecting from at least one actigraphy device, actigraphy data from the user;
      monitoring one or more of the stimulation, actigraphy data, or physiological responses;
      determining one or more of the stimulation, actigraphy data, or physiological responses exceeds a threshold;
      augmenting the actigraphy data based at least in part on the threshold; and
      collecting physiological responses of the user;
      modifying, as a second increasing intensity of stimulation, the stimulation by increasing one or more of a volume or intensity of stimulation without changing the sleep pattern;
      applying the second increasing intensity of simulation for a one to five seconds;
      determining one or more of a change in heart rate or a change in breathing, and
   in response to changes in the actigraphy data and physiological responses:
      determining a current sleep phase of the user based at least in part on the current intensity of the increasing intensity of stimulation; and
      stopping, based at least in part on the one or more of the change in heart rate or the change in breathing, the increasing intensity of the stimulation.

2. The method according to claim 1, further comprising:
   causing the at least one stimulation device to direct a subsequent increasing intensity of stimulation towards the user, the subsequent increasing intensity of stimulation determined, at least in part, on the sleep phase;
   collecting from the at least one actigraphy device, subsequent actigraphy data from the user;
   collecting subsequent physiological responses of the user to the subsequent stimulation; and
   determining a subsequent sleep phase of the user employing the subsequent physiological responses, and the subsequent actigraphy data,
   wherein the actigraphy data and subsequent actigraphy data are stored in bins of 30-60 seconds.

3. The method according to claim 1, further comprising determining when the user changes between two sleep phases, employing, at least in part, data collected during prior sleep sessions.

4. The method according to claim 1, wherein the stimulation further comprises one or more of electrical stimulation or transcranial stimulation,
   the method further comprising: applying a subsequent increasing intensity of stimulation to the user to cause a subsequent physiological response, the subsequent stimulation based upon the user's sleep phase.

5. The method according to claim 1, further comprising modifying the increasing intensity of stimulation based on time spent in a sleep phase.

6. The method according to claim 1, further comprising modifying the increasing intensity of stimulation when the actigraphy data indicates that the user is changing sleep phases.

7. The method according to claim 1, further stopping the increasing intensity of stimulation when the actigraphy data indicates that the user is waking.

8. The method according to claim 1, wherein the stimulation comprises a plurality of stimulations.

9. The method according to claim 1, wherein the stimulation comprises a plurality of stimulations and one of the plurality of stimulations comprises at least one inactive stimulation.

10. The method according to claim 1, wherein the sleep phase may comprise at least one of the following:
   a. rapid eye movement sleep phase (REM);
   b. Non-REM Stage 1 (N1) light sleep phase;
   c. Non-REM Stage 1 (N2) intermediate sleep phase;
   d. Non-REM Stage 1 (N3) deep sleep phase; and
   e. an awake phase.

11. The method according to claim 1, wherein the physiological responses comprises a change in body temperature, wherein a declining body temperature is indicative of a progression to a deeper sleep stage.

12. The method according to claim 1, wherein the physiological responses comprise at least one of the following:
   a. sound data;
   b. breathing rate data;
   d. blood pressure data;
   f. blood oxygenation data;
   g. perspiration data;
   j. location data; and
   k. a combination thereof.

13. The method according to claim 1, wherein the at least one stimulation device comprises an auditory device and a tactile stimulation device.

14. The method according to claim 1, wherein the stimulation further comprises at least one of the following:
   a neuro-stimulation comprising a transcranial stimulation or
   electrical stimulation.

15. The method of claim 1, further comprising:
   determining, based at least in part on the actigraphy data, an activity period of each minute of actigraphy data associated with a largest integrated acceleration;
   determining, as a number of counts and based at least in part on the activity period, a maximum number of zero-crossings for each minute of actigraphy data, wherein the zero-crossings are the actigraphy data crossing a zero value of actigraphy with respect to time; and
   determining a logistic regression of a weighted average of the number of counts; and
determining, based at least in part on the logistic regression, whether the user is asleep or awake.

16. A system for determining a sleep phase comprising:
   one or more processors; and
   one or more non-transitory computer readable media having instructions stored thereon which, when executed by the one or more processors, cause the one or more processors to perform operations comprising:
   estimating an initial sleep phase;
   determining an inactivity period;
   causing at least one stimulation device to direct an increasing intensity of stimulation towards a user in response to the inactivity period, wherein the stimulation is:
      determined, at least in part, by the initial sleep phase to induce a micro-arousal without altering a sleep pattern associated with the initial sleep phase; and
      applied externally as at least one of a tactile stimulation and an auditory stimulation;
   in response to the increasing intensity of stimulation:
      collecting from at least one actigraphy device, actigraphy data from the user; and
      collecting physiological responses of the user; and
   in response to changes in the actigraphy data and physiological responses:
      determining a current sleep phase of the user based at least in part on the current intensity of the increasing intensity of stimulation; and
      stopping the increasing intensity of the stimulation,
   wherein determining the current sleep phase comprises:
      determining, based at least in part on the actigraphy data, an activity period of each minute of actigraphy data associated with a largest integrated acceleration;
      determining, as a number of counts and based at least in part on the activity period, a maximum number of zero-crossings for each minute of actigraphy data, wherein the zero-crossings are the actigraphy data crossing a zero value of actigraphy with respect to time;
      determining a weighted average of the number of counts; and
      determining, based at least in part on the weighted average, whether the user is asleep or awake.

17. The system of claim 16,
   wherein the activity period is ten seconds,
   wherein the weighted average comprises a weighted average of:
      a first number of counts, A-4, associated with a first minute four minutes before a current minute,
      a second number of counts, A-3, associated with a second minute three minutes before the current minute,
      a third number of counts, A-2, associated with a third minute two minutes before the current minute,
      a fourth number of counts, A-1, associated with a fourth minute one minute before the current minute,
      a fifth number of counts, A0, associated with the current minute,
      a sixth number of counts, A+1, associated with a sixth minute one minute after the current minute, and
      a seventh number of counts, A+2, associated with a seventh minute two minutes after the current minute.

18. The system of claim 17, the operations further comprising determining a logistic regression of the weighted average,
   wherein determining whether the user is asleep or awake is further based at least in part on the logistic regression, and
   wherein determining the logistic regression comprises:
      determining, as a sum, S, 0.010(A-4)+0.015(A-3)+0.28(A-2)+0.031(A-1)+0.085(A0)+0.015(A+1)+0.010(A+2); and
      determining, as the logistic regression, a product of S and a polynomial scalar, P, and
   wherein determining whether the user is awake comprises determining the logistic regression is greater than one, the method further comprising:

determining, as a circadian amplitude, a ratio of an average activity during wakeful periods and an average activity during restful periods.

19. The system of claim 16, the operations further comprising:
monitoring one or more of the stimulation, actigraphy data, or physiological responses;
determining one or more of the stimulation, actigraphy data, or physiological responses exceeds a threshold; and
augmenting the actigraphy data based at least in part on the threshold.

* * * * *